(12) United States Patent
Kato

(10) Patent No.: US 10,365,478 B2
(45) Date of Patent: Jul. 30, 2019

(54) ENDOSCOPE OPTICAL ADAPTER AND ENDOSCOPE

(71) Applicant: OLYMPUS CORPORATION, Tokyo (JP)

(72) Inventor: Takahiko Kato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 15/378,683

(22) Filed: Dec. 14, 2016

(65) Prior Publication Data

US 2018/0164582 A1 Jun. 14, 2018

(51) Int. Cl.
| | |
|---|---|
| *G02B 27/00* | (2006.01) |
| *A61B 1/00* | (2006.01) |
| *A61B 1/12* | (2006.01) |
| *G02B 23/24* | (2006.01) |
| *A61B 1/005* | (2006.01) |
| *A61B 1/07* | (2006.01) |
| *G02B 7/14* | (2006.01) |

(52) U.S. Cl.
CPC ...... *G02B 27/0006* (2013.01); *A61B 1/00096* (2013.01); *A61B 1/00101* (2013.01); *A61B 1/00163* (2013.01); *A61B 1/127* (2013.01); *G02B 7/14* (2013.01); *G02B 23/2423* (2013.01); *G02B 23/2476* (2013.01); *A61B 1/00039* (2013.01); *A61B 1/00048* (2013.01); *A61B 1/0052* (2013.01); *A61B 1/07* (2013.01)

(58) Field of Classification Search
CPC .... G02B 27/0006; G02B 7/14; G02B 23/243; G02B 23/2476; A61B 1/00163; A61B 1/00096; A61B 1/00101; A61B 1/00126; A61B 1/127; A61B 1/0676; A61B 1/00091; A61B 1/015; A61B 1/0008; A61B 90/70
USPC ................................. 359/507, 509, 511, 513
See application file for complete search history.

(56) References Cited

U.S. PATENT DOCUMENTS

| | | | | |
|---|---|---|---|---|
| 5,339,800 | A | * 8/1994 | Wiita | A61B 1/00091 600/109 |
| 5,575,756 | A | * 11/1996 | Karasawa | A61B 1/00068 600/121 |
| 6,142,932 | A | * 11/2000 | Morizumi | A61B 1/00091 348/47 |

FOREIGN PATENT DOCUMENTS

| | | |
|---|---|---|
| JP | 2008-272168 A | 11/2008 |
| JP | 2010-200944 A | 9/2010 |
| JP | 2010200944 A * | 9/2010 |
| JP | 2014-203064 A | 10/2014 |

* cited by examiner

*Primary Examiner* — Jade R Chwasz
(74) *Attorney, Agent, or Firm* — Scully, Scott, Murphy & Presser, P.C.

(57) ABSTRACT

An endoscope optical adapter includes an objective lens for observation, a lens frame configured to hold the objective lens, and a cover member fixed to an outer circumference of the lens frame and extended to an inner side to surround the objective lens. A path for discharging a droplet adhering to the objective lens is provided at a distal end portion of the lens frame or a distal end portion of the cover member.

11 Claims, 16 Drawing Sheets

US 10,365,478 B2

ENDOSCOPE OPTICAL ADAPTER AND ENDOSCOPE

STATEMENT REGARDING PRIOR DISCLOSURES

Japanese Patent Application Laid-Open Publication No. 2016-118588 was published on Jun. 30, 2016 from Japanese Patent Application No. 2014-256455, less than 1 year before the effective filing date of the claimed invention. The disclosure in Japanese Patent Application Laid-Open Publication No. 2016-118588 was made by Takahiko KATO, who is the sole inventor of Japanese Patent Application No. 2014-256455.

Therefore, the exception under 35 U.S.C. 102(b)(1)(A) applies to disqualify Japanese Patent Application Laid-Open Publication No. 2016-118588 as prior art under 35 U.S.C. 102(a)(1).

BACKGROUND OF THE INVENTION

1. Field of the Invention

The present invention relates to an endoscope optical adapter that can discharge a droplet adhering to an objective lens and an endoscope.

2. Description of the Related Art

Endoscope apparatuses have been widely used in an industrial field and a medical field. A general endoscope apparatus includes an insertion section inserted into an observation target object and a main body section including a display section that displays an endoscopic image, which is an observation image obtained by picking up an image inside the target object. In the industrial field, the endoscope apparatus is used to observe and inspect scratches and corrosion of insides of a boiler, a turbine, an engine, and the like with an elongated insertion section of the endoscope apparatus inserted into the insides.

In an industrial endoscope, an optical adapter detachably attachable to a distal end portion of the endoscope is present. A plurality of kinds of optical adapters are present. It is possible to change a view angle and an observation direction by attaching the respective kinds of optical adapters to the distal end portion.

The industrial endoscope is often used when an inside of an engine applied with oil or the like is observed. When the inside of the engine is observed, the oil sometimes adheres to a surface of an objective lens of the optical adapter. In particular, when a gear box and the like of an engine for wind power generation are observed, the oil more often adheres to the surface of the objective lens of the optical adapter. When the oil adheres to the surface of the objective lens once, an observation image becomes unclear. Therefore, inspection is interrupted to clean a distal end portion of the optical adapter every time the oil adheres to the surface of the objective lens.

In a medical endoscope, when body fluid or the like adheres to an objective lens, as in an endoscope disclosed in Japanese Patent No. 3583542, it is possible to eject gas or liquid from an air/water feeding nozzle provided at an endoscope distal end portion to remove the body fluid.

In an endoscope disclosed in Japanese Patent Application Laid-Open Publication No. 2010-200944, an air/water feeding function and heat radiation fins are combined to efficiently cool an endoscope distal end portion and, at the same time, a droplet on an objective lens is absorbed among the heat radiation fins by capillary action of gaps of the heat radiation fins to prevent the droplet from remaining on the objective lens.

SUMMARY OF THE INVENTION

An endoscope optical adapter according to an aspect of the present invention includes: an objective lens for observation; a lens frame configured to hold the objective lens; a cover member fixed to an outer circumference of the lens frame and extended to an inner side to surround the objective lens; and an attaching and detaching member provided with a screw mechanism, the attaching and detaching member being coupled to a proximal end side of the lens frame and detachably attachable to a distal end portion of an endoscope. A path for discharging a droplet adhering to the objective lens is provided at a distal end portion of the lens frame or a distal end portion of the cover member.

An endoscope according to an aspect of the present invention includes: an objective lens for observation; a lens frame configured to hold the objective lens; and a cover member fixed to an outer circumference of the lens frame and extended to an inner side to surround the objective lens. A path for discharging a droplet adhering to the objective lens is provided at a distal end portion of the lens frame or a distal end portion of the cover member.

DETAILED DESCRIPTION OF THE PREFERRED EMBODIMENTS

Embodiments of the present invention are explained below with reference to the drawings.

First Embodiment

Figure 1:
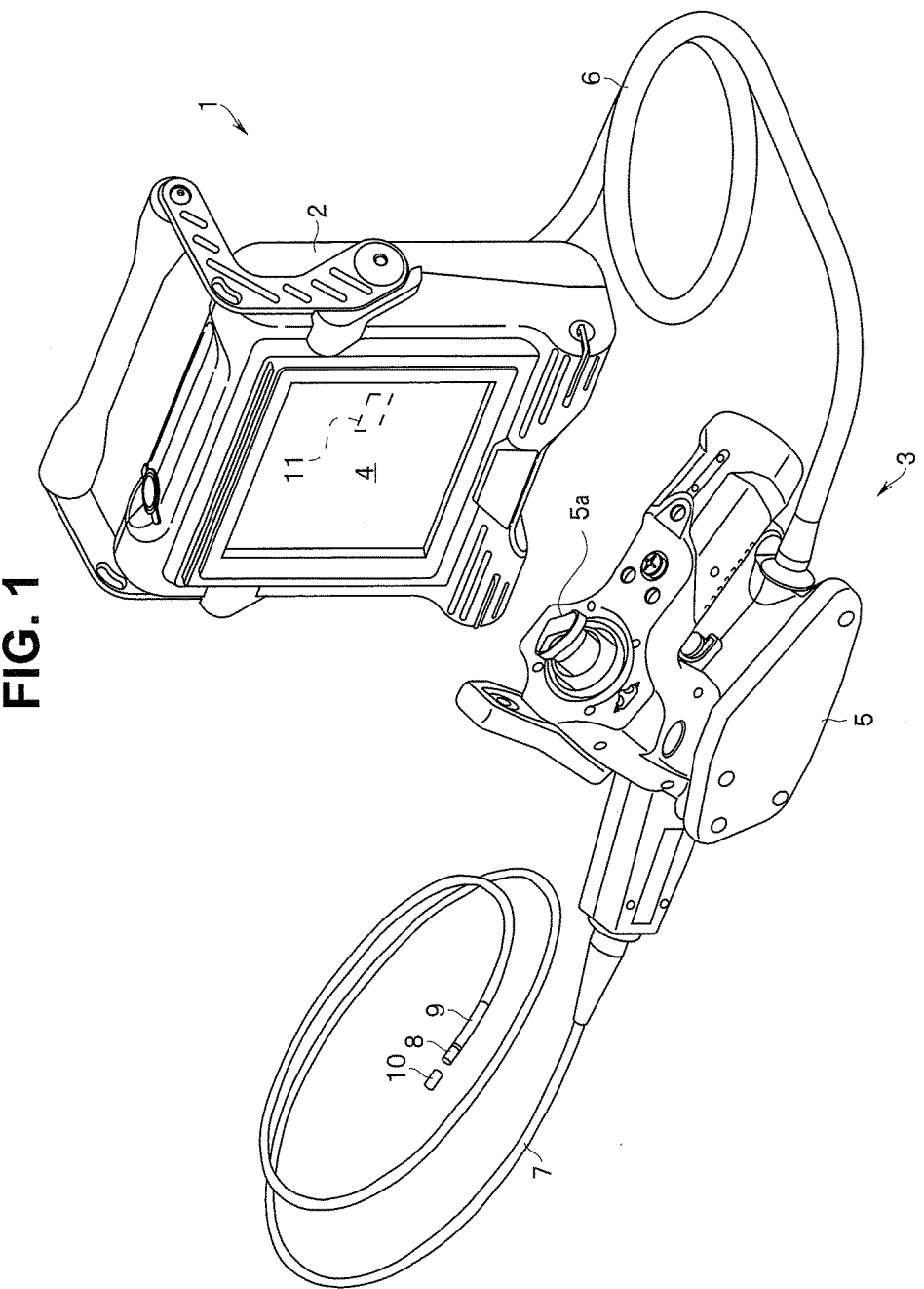
FIG. 1 is an exterior view of an endoscope apparatus according to a first embodiment.
Figure 2:
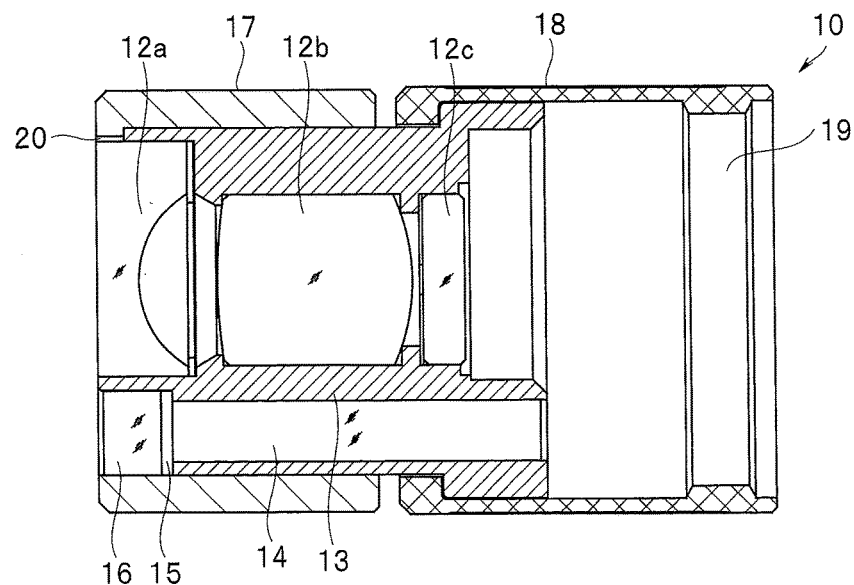
FIG. 2 is a perspective view showing a configuration of an optical adapter in the first embodiment.
Figure 3:
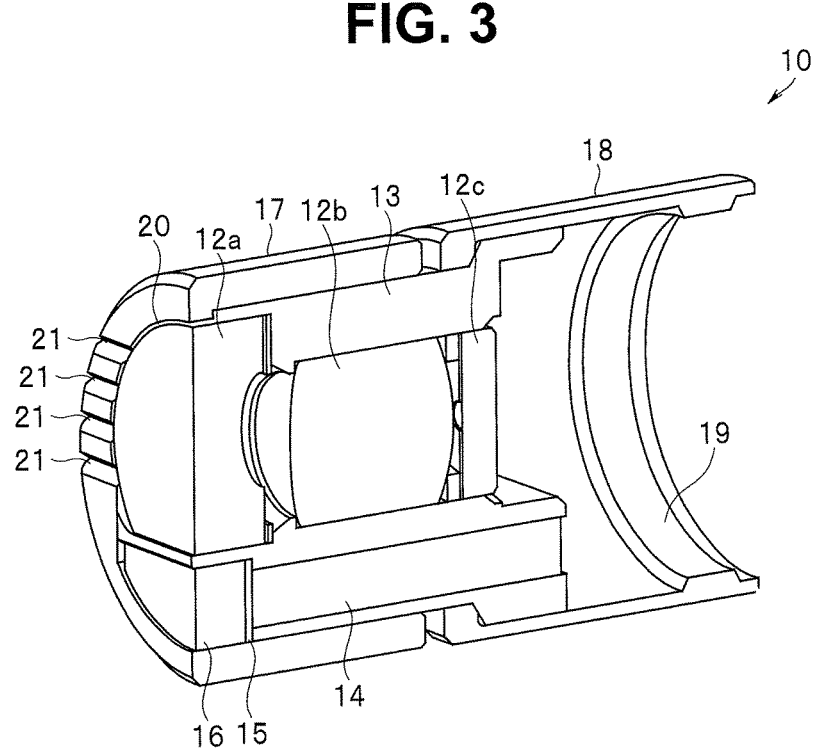
FIG. 3 is a sectional perspective view showing the configuration of the optical adapter in the first embodiment.
Figure 4:
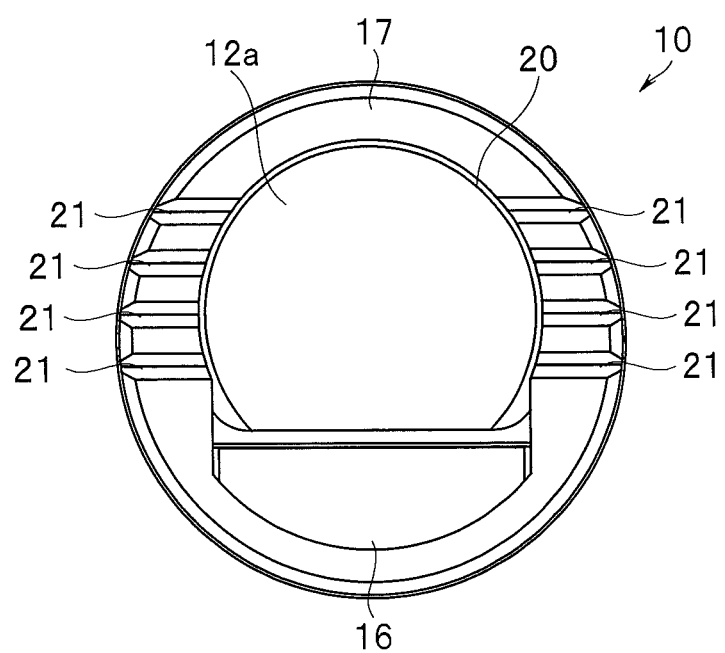
FIG. 4 is a front view showing the configuration of the optical adapter in the first embodiment.

First, a configuration of an endoscope apparatus in a first embodiment of the present invention is explained with reference to FIGS. 1 to 4. FIG. 1 is an exterior view of the endoscope apparatus according to the first embodiment. FIG. 2 is a perspective view showing a configuration of an optical adapter in the first embodiment. FIG. 3 is a sectional perspective view showing the configuration of the optical adapter in the first embodiment. FIG. 4 is a front view showing the configuration of the optical adapter in the first embodiment.

As shown in FIG. 1, an endoscope apparatus 1 includes a main body section 2, which is a main unit, and a scope unit (an endoscope) 3 connected to the main body section 2. The main body section 2 includes a liquid crystal panel (hereinafter abbreviated as LCD) 4 functioning as a display device on which an endoscopic image, an operation menu, and the like are displayed. The LCD 4 is a display section that displays an endoscopic image. A touch panel may be provided in the LCD 4.

The scope unit 3 includes an operation section 5, a universal cable 6 that connects the operation section 5 and the main body section 2, and an insertion section 7 consisting of a flexible insertion tube. The scope unit 3 is detachably attachable to the main body section 2 via the universal cable 6.

A not-shown image pickup unit is incorporated in a distal end portion 8 of the insertion section 7. The image pickup unit is configured from an image pickup device such as a CCD sensor or a CMOS sensor and an image pickup optical system such as a lens disposed on an image pickup surface side of the image pickup device. A bending section 9 is provided on a proximal end side of the distal end portion 8. An optical adapter 10, which is an endoscope optical adapter, is attachable to the distal end portion 8. Various operation buttons such as a freeze button and a recording instruction button are provided in the operation section 5.

A user can operate the various operation buttons of the operation section 5 to perform image pickup of an object, moving image recording, still image recording, and the like. The user can operate a bending button 5a for upward, downward, left, and right (U/D/L/R) directions to bend the bending section 9 in a desired direction. Further, in the case of a configuration in which the touch panel is provided in the LCD 4, the user can also operate the touch panel to instruct various kinds of operation of the endoscope apparatus 1.

Image data of an endoscopic image obtained by image pickup is inspection data of an inspection target. The image data is recorded in a memory card 11, which is a recording medium. The memory card 11 is detachably attachable to the main body section 2. Note that, although the image data is recorded in the memory card 11, the image data may be recorded in a not-shown memory incorporated in the main body section 2.

As shown in FIGS. 2 and 3, the optical adapter 10 includes a lens frame 13 that holds a plurality of objective lenses 12a, 12b, and 12c for observation. The lens frame 13 holds the objective lenses 12a, 12b, and 12c in order from a distal end side. However, the number and the order of objective lenses held by the lens frame 13 are not limited to the number and the order shown in FIG. 2.

The lens frame 13 is formed of a metal member such as stainless steel. An illumination optical system 14 such as a light guide, which guides illumination light, is inserted through the lens frame 13. A diffusing member 15 such as a glass bead for diffusing the guided illumination light is provided on a distal end face of the illumination optical system 14. A cover glass 16 is disposed on the distal end side of the diffusing member 15.

A substantially cylindrical cover member 17 for covering the lens frame 13 is provided on an outer circumference of the lens frame 13. The cover member 17 is formed of a metal member such as stainless steel and fixed to the lens frame 13 by an adhesive, a screw member, or the like.

The proximal end side of the lens frame 13 is coupled to the distal end side of a retaining ring 18 formed of a metal member such as stainless steel. For example, a not-shown screw mechanism is provided on the proximal end side of the lens frame 13 and the distal end side of the retaining ring 18. The lens frame 13 is coupled to the retaining ring 18 by the screw mechanism. A screw mechanism 19 is provided on the proximal end side of the retaining ring 18, which is an attaching and detaching member. The retaining ring 18 is configured to be detachably attachable to the distal end portion 8 of the scope unit 3 via the screw mechanism 19.

As shown in FIGS. 2 to 4, a distal end portion of the cover member 17 is extended to an inner side to surround the objective lens 12a. An opening having a diameter larger than a hole diameter of the lens frame, in which the objective lens 12a is fit, is provided in a distal end face of the cover member 17. That is, a gap 20 is formed between the objective lens 12a and the cover member 17. As shown in FIG. 4, the gap 20 is provided over a half circumference or more of a peripheral section of the objective lens 12a. Note that the gap 20 may be provided over an entire circumference of the peripheral section of the objective lens 12a.

As shown in FIGS. 3 and 4, a plurality of grooves 21 having a V shape are provided from an inner circumference to an outer circumference on the distal end face of the cover member 17. The plurality of grooves 21 are provided to be deeper than the distal end face of the objective lens 12a.

The plurality of grooves 21 are provided around the gap 20 between the objective lens 12a and the cover member 17. That is, the plurality of grooves 21 are provided in the peripheral section of the objective lens 12a and are not provided in a peripheral section of the cover glass 16. A plurality of grooves are not provided in the peripheral section of the cover glass 16 in this way in order to prevent the illumination light guided by the illumination optical system 14 from being irregularly reflected by liquid or the like accumulated in the grooves. Note that a shape of the plurality of grooves 21 is not limited to the V shape and may be, for example, a rectangular shape or a semicircular shape. The plurality of grooves 21 are provided in a lateral direction in an example shown in FIG. 4. However, the plurality of grooves 21 are not limited to this and may be provided in other directions.

Action of the optical adapter 10 configured in this way is explained.

Figure 5A:
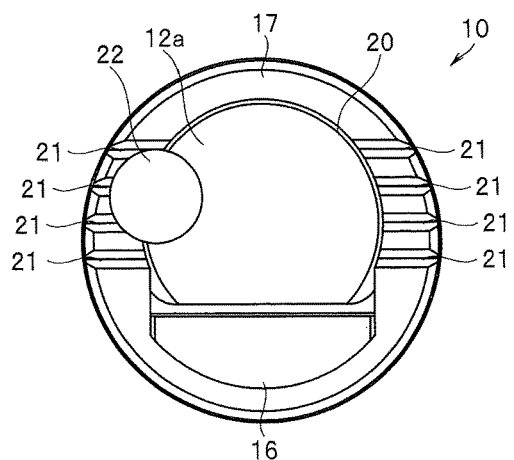
FIG. 5A is a diagram for explaining action at the time when a droplet adheres to an optical adapter 10.
Figure 5B:
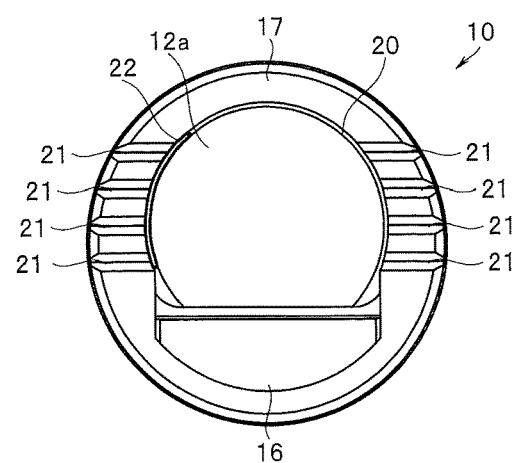
FIG. 5B is a diagram for explaining the action at the time when the droplet adheres to the optical adapter 10.
Figure 5C:
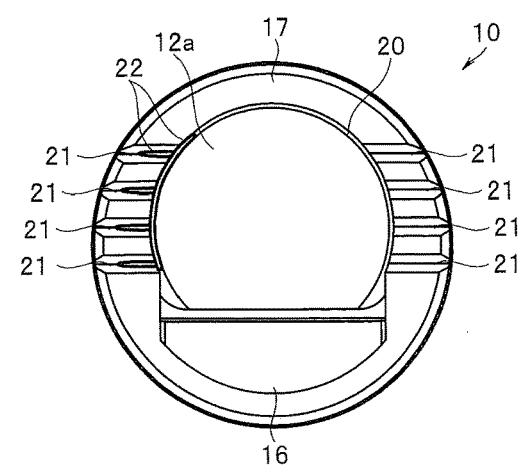
FIG. 5C is a diagram for explaining the action at the time when the droplet adheres to the optical adapter 10.

FIGS. 5A, 5B, and 5C are diagrams for explaining action at the time when a droplet adheres to the optical adapter 10.

When an operator attaches the optical adapter 10 to the distal end portion 8 of the scope unit 3 and performs an endoscopic inspection of an inspection target object such as an engine for wind power generation, as shown in FIG. 5A, a droplet 22 such as oil adheres to the objective lens 12a.

In the present embodiment, the gap 20 is provided between the objective lens 12a and the cover member 17 of the optical adapter 10. Therefore, when the droplet 22 such as oil adheres to the objective lens 12a, as shown in FIG. 5B, the droplet 22 is sucked up to the gap 20 by capillary action.

When a constant amount or more of the liquid accumulates in the gap 20, as shown in FIG. 5C, the liquid is discharged from the gap 20 to the plurality of grooves 21 by capillary action of the plurality of grooves 21 provided on the distal end face of the cover member 17. When a constant amount or more of the liquid further accumulates in the plurality of grooves 21, the liquid is discharged from a side surface side of the cover member 17.

In this way, in the optical adapter 10 attached to the distal end portion 8 of the scope unit 3 in the present embodiment, the gap 20 is provide between the objective lens 12a and the cover member 17 and the droplet 22 adhering to the objective lens 12a is sucked into the gap 20 by the capillary action. Further, by providing the plurality of grooves 21 on the distal end face of the cover member 17, the liquid accumulated in the gap 20 can be discharged to an outside of the cover member 17 by the capillary action. As a result, even when a large amount of oil or the like adheres to the objective lens 12a, the oil or the like can be discharged to the outside of the cover member 17 via the gap 20 and the plurality of grooves 21. Therefore, it is possible to perform satisfactory observation of an endoscopic image.

Note that a structure of the optical adapter 10 explained above may be applied to the distal end portion 8 of the scope unit 3. That is, even in the scope unit 3 to which the optical adapter 10 is not attachable, by applying the structure of the optical adapter 10 to the distal end portion 8, it is possible to surely remove a large amount of oil or the like adhering to an objective lens provided at the distal end portion 8.

Therefore, with the endoscope and the endoscope adapter in the present embodiment, even when a droplet such as a large amount of oil adheres to the objective lens, it is possible to surely remove the droplet adhering to the objective lens.

(Modification 1)

A modification 1 of the first embodiment is explained.

Figure 6:
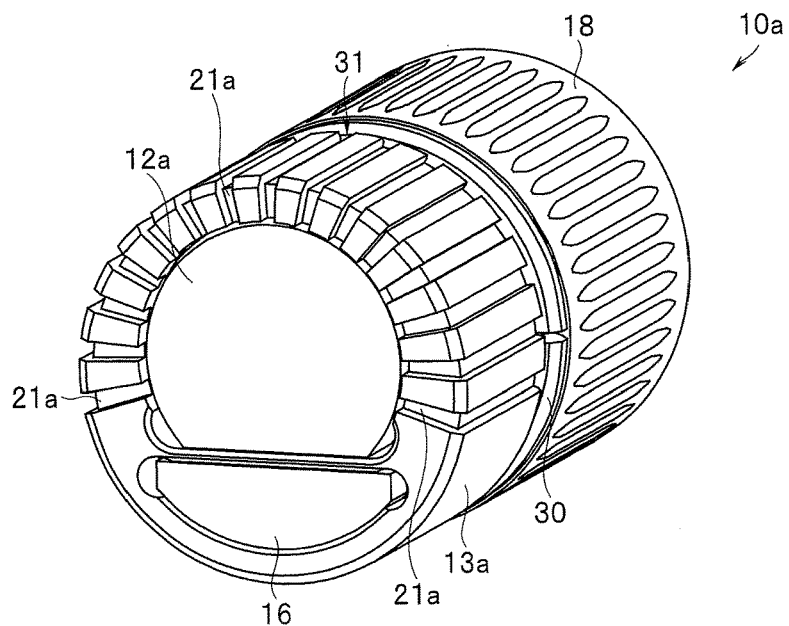
FIG. 6 is a perspective view showing a configuration of an optical adapter in a modification 1 of the first embodiment.
Figure 7:
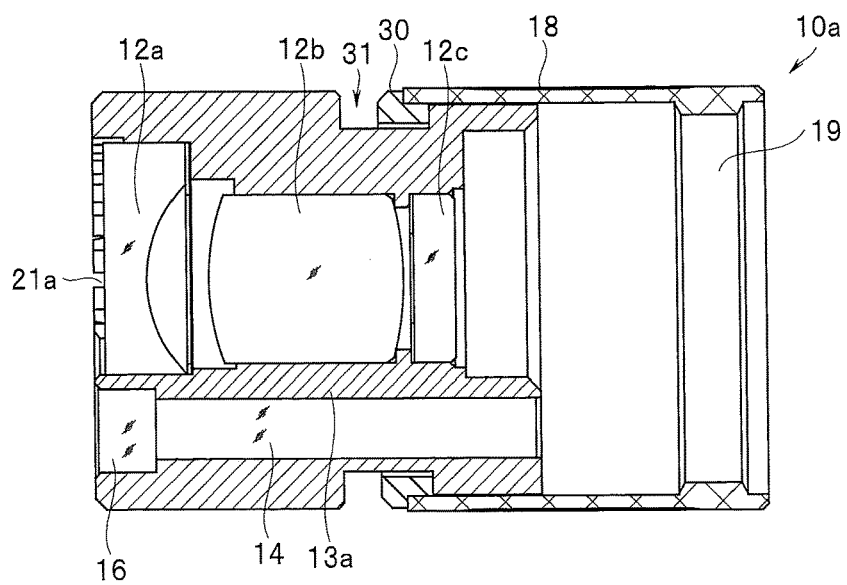
FIG. 7 is a sectional view showing the configuration of the optical adapter in the modification 1 of the first embodiment.

FIG. 6 is a perspective view showing a configuration of an optical adapter in a modification 1 of the first embodiment. FIG. 7 is a sectional view showing the configuration of the optical adapter in the modification 1 of the first embodiment. Note that, in FIGS. 6 and 7, components same as the components shown in FIGS. 2 to 4 are denoted by the same reference numerals and signs and explanation of the components is omitted.

As shown in FIGS. 6 and 7, an optical adapter 10a in the modification 1 includes a lens frame 13a in which the lens frame 13 and the cover member 17 shown in FIG. 2 are integrated. In the optical adapter 10a, the diffusing member 15 shown in FIG. 2 is deleted.

A C-shaped ring 30 is attached to the proximal end side of the lens frame 13a. The retaining ring 18 is welded to the C-shaped ring 30 by laser welding. A gap 31 is provided between the lens frame 13a and the retaining ring 18.

A plurality of grooves 21a having a tapered shape, that is, increasing in width of the groove from an inner circumference to an outer circumference are provided on a distal end face of the lens frame 13a. The plurality of grooves 21a are extended to the proximal end side in an insertion axis direction of a side surface of the lens frame 13a. By forming the plurality of grooves 21a in the tapered shape in this way, it is possible to increase an effect of the capillary action. Note that the plurality of grooves 21 provided in the cover member 17 in the first embodiment explained above may be formed in the tapered shape as in this modification.

Action of the optical adapter 10a configured in this way is explained.

When a droplet such as oil adheres to the objective lens 12a of the optical adapter 10a, the droplet is sucked up to the plurality of grooves 21a by the capillary action. Since the plurality of grooves 21a are provided on the distal end face and the side surface of the lens frame 13a, when a constant amount or more of the droplet adheres to the objective lens 12a, the droplet is sucked up to the plurality of grooves 21a provided on the distal end face and the side surface of the lens frame 13a.

Since the plurality of grooves 21a are extended to the proximal end side of the side surface of the lens frame 13a, when the constant amount or more of the droplet adheres to the objective lens 12a, liquid sucked up by the capillary action is discharged to the gap 31 provided between the lens frame 13a and the retaining ring 18.

In this way, in the optical adapter 10a, the plurality of grooves 21a are provided to the proximal end side of the side surface and the gap 31 is further provided between the lens frame 13a and the retaining ring 18. Therefore, it is possible to increase an amount of a droplet sucked up by the capillary action.

Therefore, with the optical adapter 10a in the modification 1, it is possible to remove a larger amount of the droplet than the optical adapter 10 in the first embodiment.

(Modification 2)

A modification 2 of the first embodiment is explained.

Figure 8:
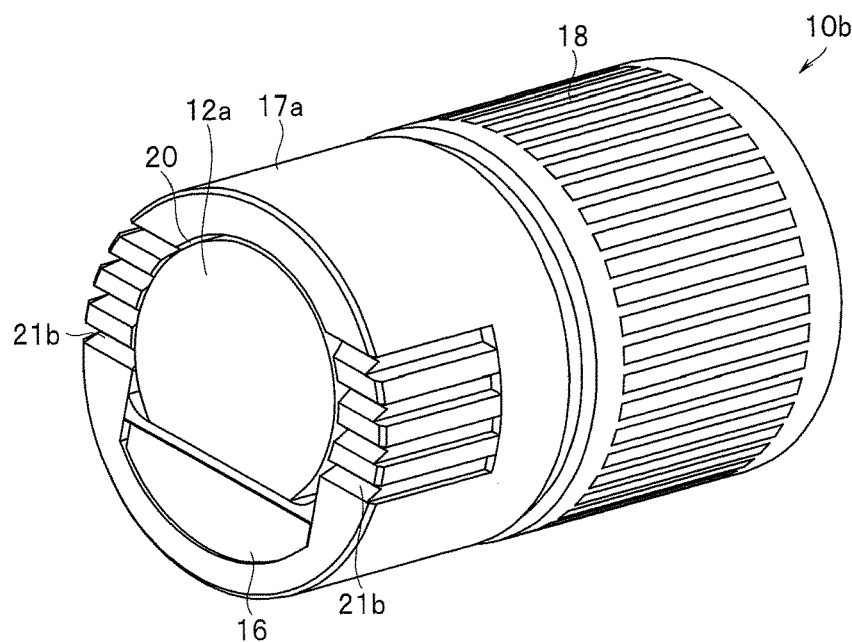
FIG. 8 is a perspective view showing a configuration of an optical adapter in a modification 2 of the first embodiment.

FIG. 8 is a perspective view showing a configuration of an optical adapter in the modification 2 of the first embodiment. Note that, in FIG. 8, components same as the components shown in FIGS. 2 to 4 are denoted by the same reference numerals and signs and explanation of the components is omitted.

An optical adapter 10b is configured using a cover member 17a instead of the cover member 17 shown in FIG. 2. A plurality of grooves 21b are provided on a distal end face of the cover member 17a. The plurality of grooves 21b are extended to a predetermined position in an insertion axis direction of a side surface of the cover member 17a.

With such a configuration, when the constant amount or more of the droplet adheres to the objective lens 12a, the liquid is sucked up, by the capillary action, to the plurality of grooves 21b extended to the predetermined position in the insertion axis direction of the side surface of the cover member 17a.

In the optical adapter 10b, by extending the plurality of grooves 21b to the predetermined position of the side surface of the cover member 17a in this way, an amount of the liquid that can be accumulated in the plurality of grooves 21b is increased.

Therefore, with the optical adapter 10b in the modification 2, it is possible to remove a larger amount of the droplet than the optical adapter 10 in the first embodiment.

Note that a configuration of the optical adapter 10b in the modification 2 is not limited to the configuration shown in FIG. 8 and may be configurations shown in FIGS. 9 and 10 below.

Figure 9:
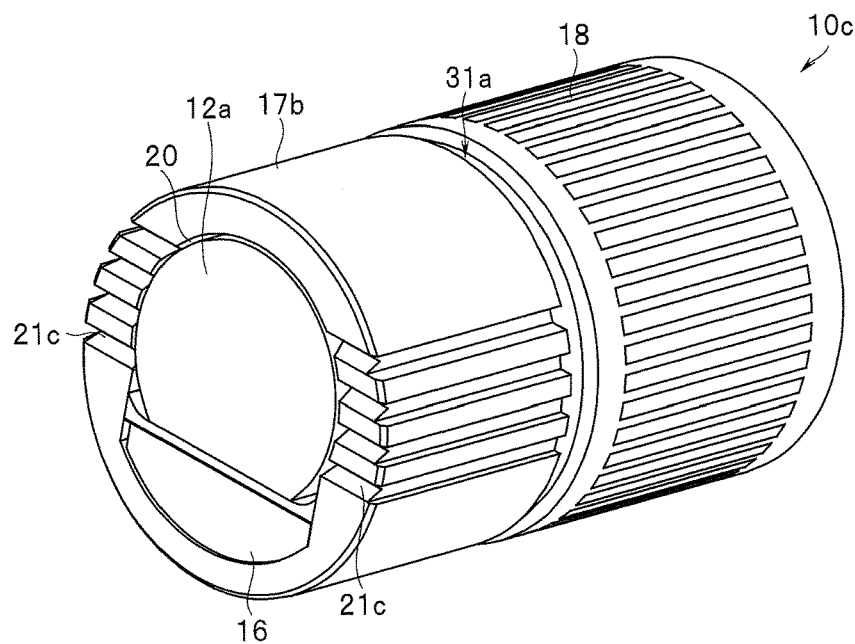
FIG. 9 is a perspective view showing another configuration of the optical adapter in the modification 2 of the first embodiment.

FIG. 9 is a perspective view showing another configuration of the optical adapter in the modification 2 of the first embodiment. Note that, in FIG. 9, components same as the components shown in FIG. 8 are denoted by the same reference numerals and signs and explanation of the components is omitted.

As shown in FIG. 9, an optical adapter 10c is configured using a cover member 17b instead of the cover member 17a shown in FIG. 8. A plurality of grooves 21c are provided on a distal end face of the cover member 17b. The plurality of grooves 21c are extended to the proximal end side in an insertion axis direction of a side surface of the cover member 17b. A gap 31a is provided between the cover member 17b and the retaining ring 18. The other components are the same as the components of the optical adapter 10b shown in FIG. 8.

With such a configuration, when a constant amount or more of the droplet adheres to the objective lens 12a, liquid is sucked up to, by the capillary action, the plurality of grooves 21c extended to the proximal end side in the insertion axis direction of the side surface of the cover member 17a. Thereafter, the liquid can be discharged to the gap 31a.

Therefore, the optical adapter 10c can remove a larger amount of the droplet than the optical adapter 10b shown in FIG. 8.

Figure 10:
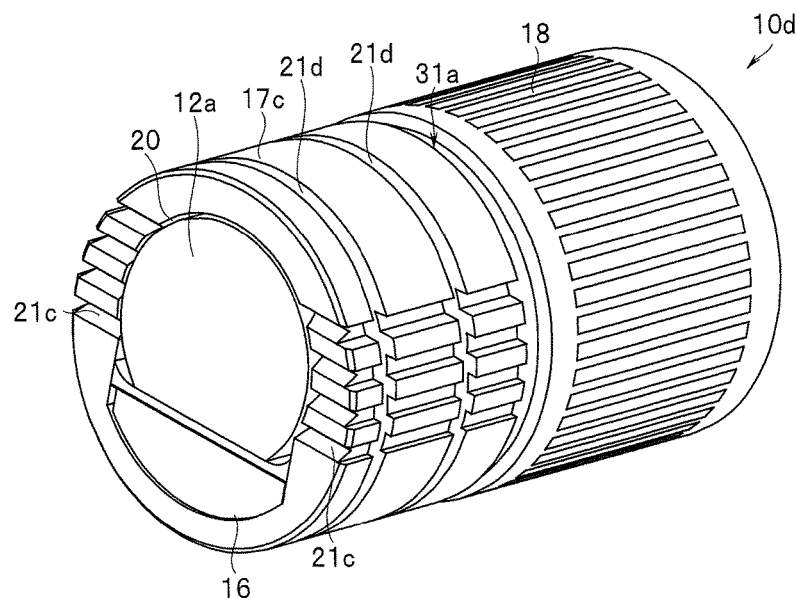
FIG. 10 is a perspective view showing another configuration of the optical adapter in the modification 2 of the first embodiment.

FIG. 10 is a perspective view showing another configuration of the optical adapter in the modification 2 of the first embodiment. Note that, in FIG. 10, components same as the components shown in FIG. 9 are denoted by the same reference numerals and signs and explanation of the components is omitted.

As shown in FIG. 10, an optical adapter 10d is configured using a cover member 17c instead of the cover member 17b shown in FIG. 9. The cover member 17c is configured by further adding a plurality of grooves 21d in a circumferential direction in the cover member 17b shown in FIG. 9. The other components are the same as the components of the optical adapter 10c shown in FIG. 9.

Figure 11:
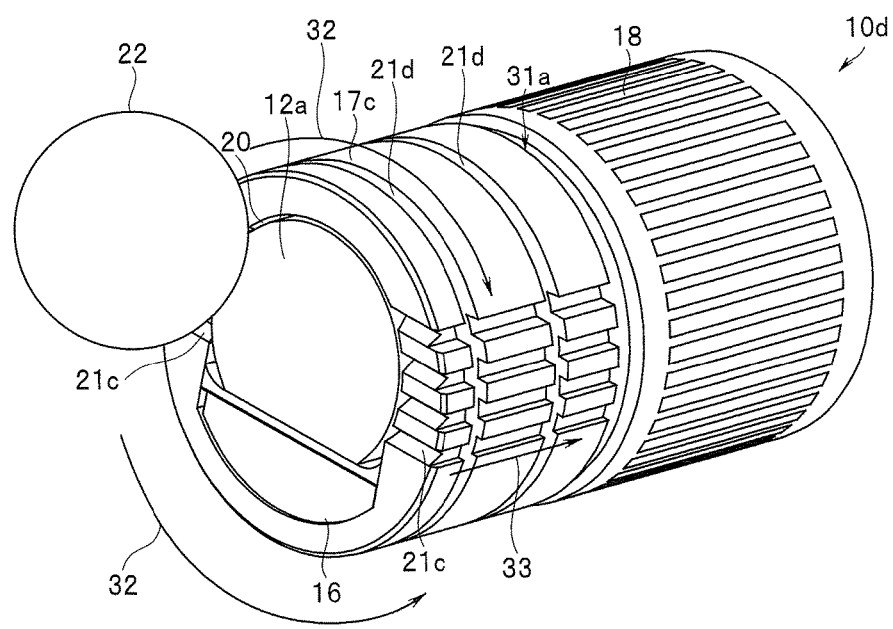
FIG. 11 is a diagram for explaining action at the time when a droplet adheres to an optical adapter 10d.

FIG. 11 is a diagram for explaining action at the time when a droplet adheres to the optical adapter 10d.

As shown in FIG. 11, when the droplet 22 adheres to a right side (a left side on FIG. 11) of the optical adapter 10d, as indicated by an arrow 32, liquid is sucked up to a left side (a right side on FIG. 11) of the optical adapter 10d by the capillary action of the plurality of grooves 21d provided in a circumferential direction of a side surface of the cover member 17c. As indicated by an arrow 33, the liquid sucked up to the left side of the optical adapter 10d is sucked up to the proximal end side of the cover member 17c by the capillary action of the plurality of grooves 21c provided in an insertion axis direction of the side surface of the cover member 17c. The liquid is discharged to the gap 31a.

In this way, in the optical adapter 10d, the plurality of grooves 21d are provided in the circumferential direction of the side surface of the cover member 17c. Therefore, the optical adapter 10d can discharge the liquid to the gap 31a also using the plurality of grooves 21c on an opposite side of a direction in which the droplet 22 adheres. That is, the optical adapter 10d can discharge liquid using the entire plurality of grooves 21c in the insertion axis direction of the side surface of the cover member 17c and plurality of grooves 21d in the circumferential direction.

Therefore, the optical adapter 10d can remove a larger amount of the droplet than the optical adapter 10c shown in FIG. 9.

(Modification 3)

A modification 3 of the first embodiment is explained.

Figure 12:
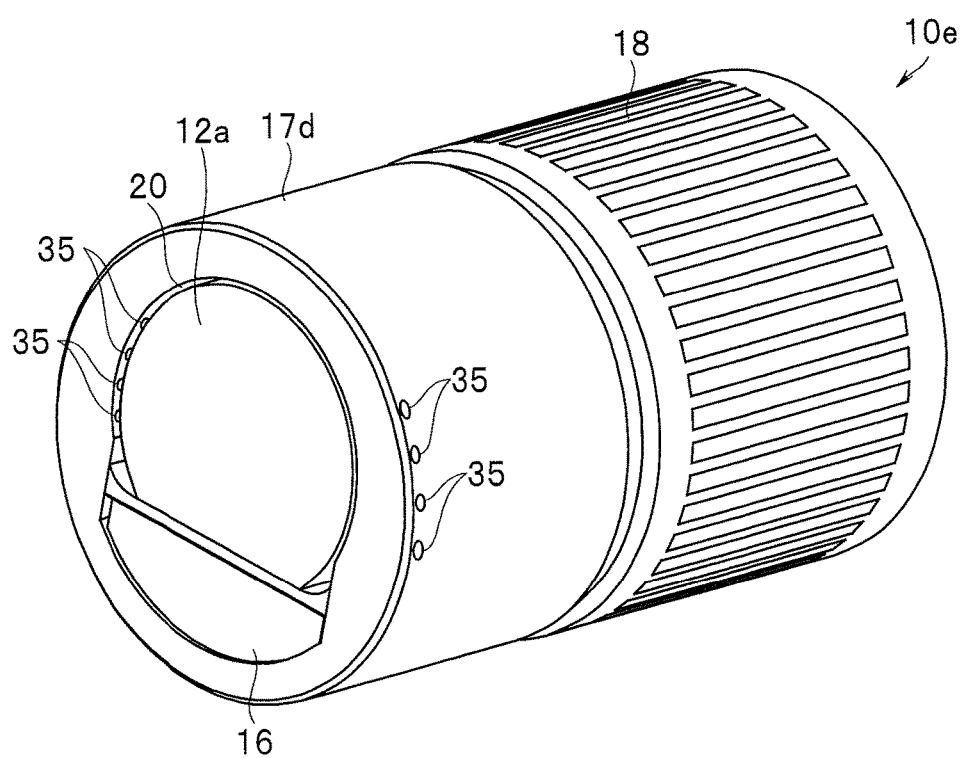
FIG. 12 is a perspective view showing a configuration of an optical adapter in a modification 3 of the first embodiment.

FIG. 12 is a perspective view showing a configuration of an optical adapter in the modification 3 of the first embodiment. In FIG. 12, components same as the components shown in FIGS. 2 to 4 are denoted by the same reference numerals and signs and explanation of the components is omitted.

As shown in FIG. 12, an optical adapter 10e is configured using a cover member 17d instead of the cover member 17 shown in FIG. 2. In the cover member 17d, a plurality of very small holes 35 piercing through the cover member 17d from an inner circumferential surface to an outer circumferential surface on the distal end side on which the objective lens 12a is disposed are provided. Note that the plurality of holes 35 are provided in a lateral direction in an example shown in FIG. 12. However, the plurality of holes 35 are not limited to this and may be provided in other directions. The other components are the same as the components of the optical adapters 10 in the first embodiment.

A droplet adhering to the objective lens 12a is sucked up to the gap 20 between the objective lens 12a and the cover member 17d by the capillary action due to the gap 20. When a constant amount or more of the droplet adheres to the objective lens 12a, the droplet is sucked up from the inner circumferential surface to the outer circumferential surface of the cover member 17d by the capillary action due to the plurality of holes 35 and discharged to a side surface of the cover member 17d.

In this way, in the optical adapter 10e, the plurality of holes 35 piercing through the cover member 17d from the inner circumferential surface to the outer circumferential surface of the cover member 17d are provided. The droplet adhering to the objective lens 12a is discharged to the side surface of the cover member 17d by the capillary action due to the plurality of holes 35. As a result, even when a large amount of the droplet adheres to the objective lens 12a, it is possible to discharge liquid to the outside of the cover member 17d.

Therefore, with the optical adapter 10e in the modification 3, it is possible to remove a larger amount of the droplet than the optical adapter 10 in the first embodiment.

(Modification 4)

A modification 4 of the first embodiment is explained.

Figure 13:
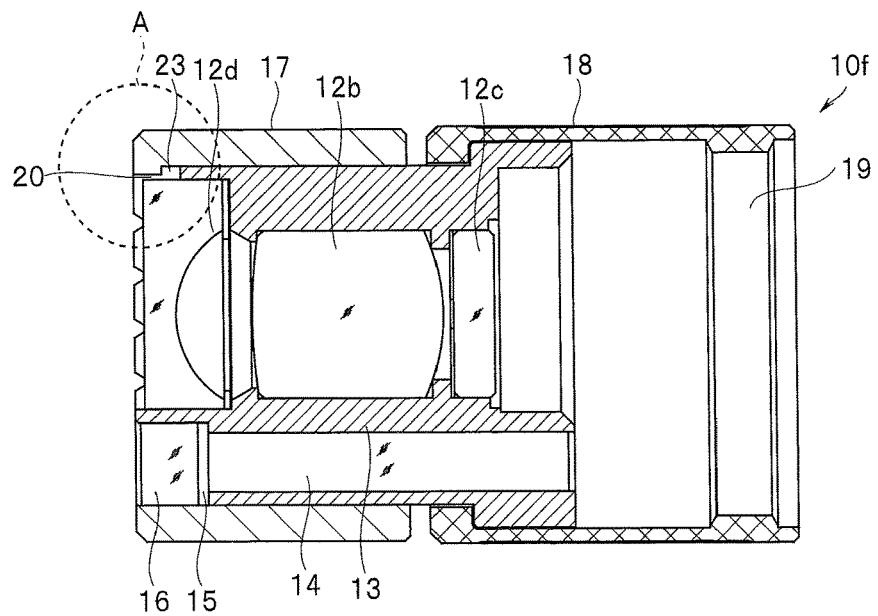
FIG. 13 is a sectional view showing a configuration of an optical adapter in a modification 4 of the first embodiment.
Figure 14:
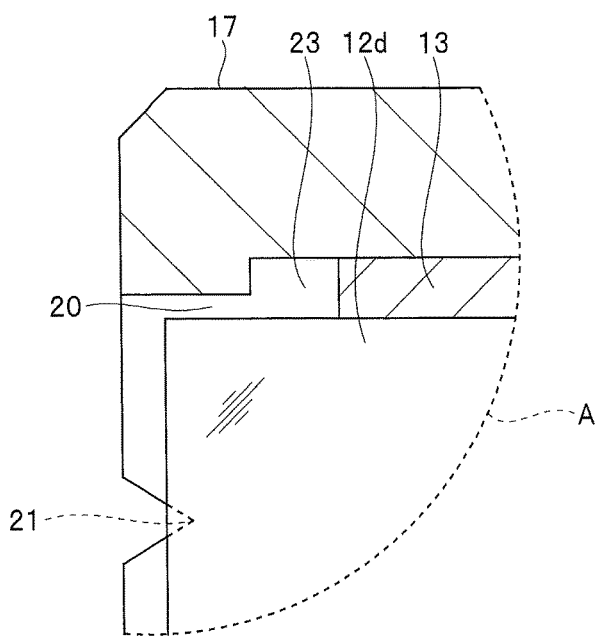
FIG. 14 is an enlarged view of an A part in FIG. 13.

FIG. 13 is a sectional view showing a configuration of an optical adapter in a modification 4 of the first embodiment. FIG. 14 is an enlarged view of an A part in FIG. 13. Note that, in FIGS. 13 and 14, components same as the components shown in FIGS. 2 to 4 are denoted by the same reference numerals and signs and explanation of the components is omitted.

As shown in FIG. 13, an optical adapter 10f is configured using an objective lens 12d instead of the objective lens 12a shown in FIG. 2. A distal end face of the objective lens 12d is configured to be disposed on the proximal end side with respect to the distal end face of the cover member 17.

The gap 20 is provided between a circumference of the objective lens 12d and the cover member 17. A space 23 formed by the distal end face of the lens frame 13 that holds the objective lens 12d, a side surface of the objective lens 12d, and an inner surface (an inner wall) of the cover member 17 communicates with the gap 20. The space 23 having a volume larger than the gap 20 is formed by the distal end face of the lens frame 13, the side surface of the objective lens 12d, and the inner surface of the cover member 17. That is, the space 23 has a space wider than the gap 20. As shown in FIG. 14, the plurality of grooves 21 provided on the distal end face of the cover member 17 are provided in positions deeper than the distal end face of the objective lens 12d.

With the configuration explained above, in the optical adapter 10f, when the droplet 22 adheres to the objective lens 12d, the droplet 22 can be sucked up to the gap 20 by the capillary action and accumulated in the space 23 that communicates with the gap 20. That is, the optical adapter 10f can remove a large amount of the droplet 22 adhering to the circumference of the objective lens 12d.

Further, since the plurality of grooves 21 are provided in the positions deeper than the distal end face of the objective lens 12d, the droplet 22 temporally accumulated in the gap 20 and the space 23 comes into contact with a part of the grooves 21 of the cover member 17 before overflowing to the distal end face of the objective lens 12d. As a result, the droplet 22 is discharged to a side surface direction by the capillary action. It is possible to always maintain satisfactory image quality.

Therefore, with the optical adapter 10f in the modification 4, it is possible to remove a larger amount of the droplet than the optical adapter 10 in the first embodiment. It is possible to always maintain satisfactory image quality.

Second Embodiment

A second embodiment is explained.

Figure 15:
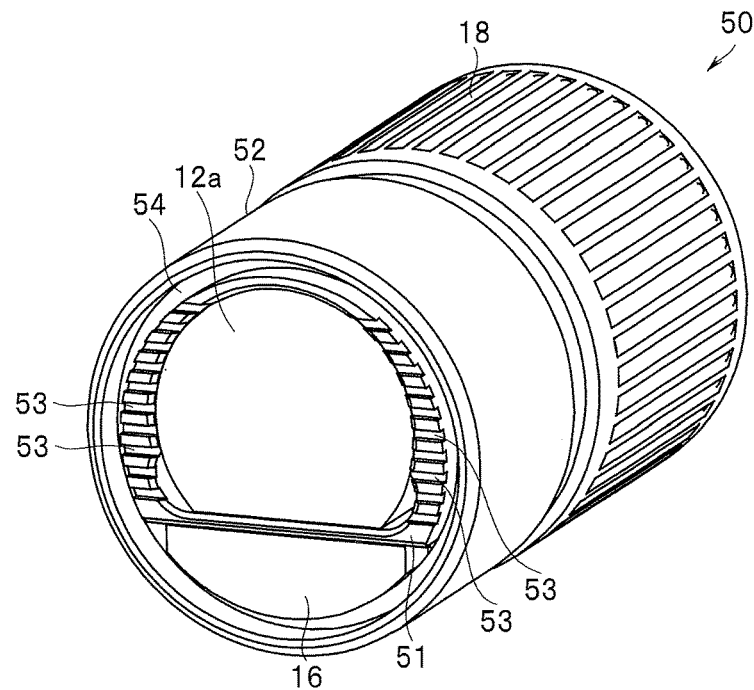
FIG. 15 is a perspective view showing a configuration of an optical adapter according to a second embodiment.
Figure 16:
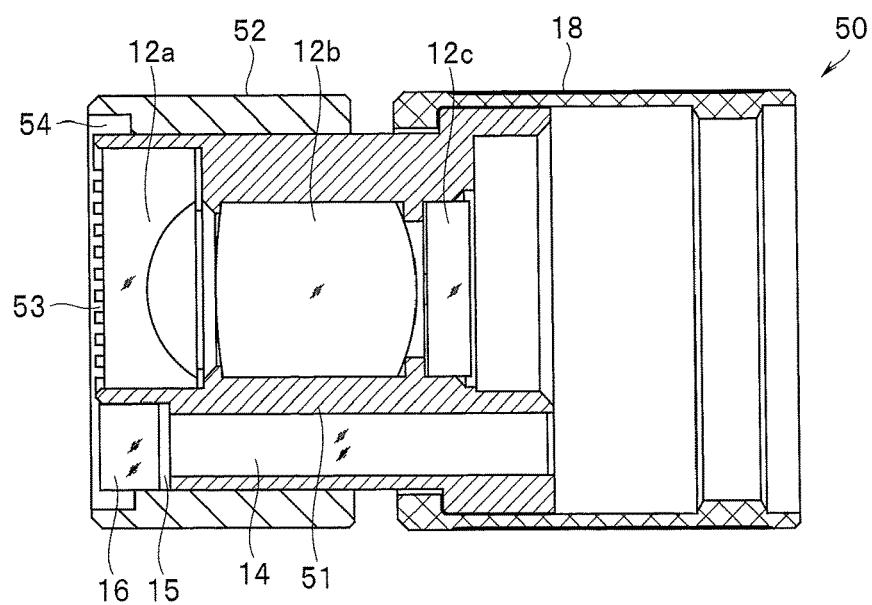
FIG. 16 is a sectional view showing the configuration of the optical adapter according to the second embodiment.

FIG. 15 is a perspective view showing a configuration of an optical adapter according to the second embodiment. FIG. 16 is a sectional view showing the configuration of the optical adapter according to the second embodiment. Note that, in FIGS. 15 and 16, components same as the components shown in FIGS. 2 to 4 are denoted by the same reference numerals and signs and explanation of the components is omitted. Explanation of a configuration of an endoscope apparatus in the present embodiment is omitted because the configuration is the same as the configuration shown in FIG. 1.

As shown in FIGS. 15 and 16, an optical adapter 50 in the present embodiment is configured using a lens frame 51 and a cover member 52 respectively instead of the lens frame 13 and the cover member 17 in the first embodiment.

In the lens frame 51, a plurality of grooves 53 are provided on a distal end face that surrounds the objective lens 12a. As in the first embodiment, a shape of the plurality of grooves 53 is a V shape, a rectangular shape, a semicircular shape, or the like and is not particularly limited. The plurality of grooves 53 are provided in a lateral direction in an example shown in FIG. 15. However, the plurality of grooves 53 are not limited to this and may be provided in other directions.

The plurality of grooves 53 are extended from an inner circumference to an outer circumference of a distal end face of the lens frame 51. A droplet adhering to the objective lens 12a is discharged to the cover member 52 side through the plurality of grooves 53 by the capillary action.

The cylindrical cover member 52 is provided on an outer circumference of the lens frame 51. The cover member 52 is fixed to the lens frame 51 by an adhesive, a screw, or the like. A space 54, in which liquid discharged by the plurality of grooves 53 can be accumulated, is provided between a distal end portion of the cover member 52 and the lens frame 51 and between the distal end portion of the cover member 52 and the cover glass 16. The other components are the same as the components of the optical adapter 10 in the first embodiment.

Action of the optical adapter 50 configured in this way is explained.

When an operator attaches the optical adapter 50 to the distal end portion 8 of the scope unit 3 and performs an endoscopic inspection of an inspection target object such as an engine for wind power generation, a droplet such as oil adheres to the objective lens 12a. The droplet adhering to the objective lens 12a is sucked up to the cover member 52 side by the capillary action due to the plurality of grooves 53 provided on the distal end face of the lens frame 51. The liquid sucked up in this way accumulates in the wide space 54 between the cover member 52 and the lens frame 51 and between the cover member 52 and the cover glass 16.

In this way, in the optical adapter 50 in the present embodiment, the plurality of grooves 53 are provided on the distal end face of the lens frame 51 and the wide space 54 between the cover member 52 and the lens frame 51 and between the cover member 52 and the cover glass 16 is provided. As a result, even when a large amount of oil or the like adheres to the objective lens 12a, a droplet can be sucked up by the capillary action due to the plurality of grooves 53 and accumulated in the space 54.

Therefore, with the endoscope and the endoscope optical adapter in the present embodiment, as in the first embodiment, even when a large amount of the droplet such as oil adheres to the objective lens, it is possible to surely remove the droplet adhering to the objective lens.

(Modification 1)

A modification 1 of the second embodiment is explained.

Figure 17:
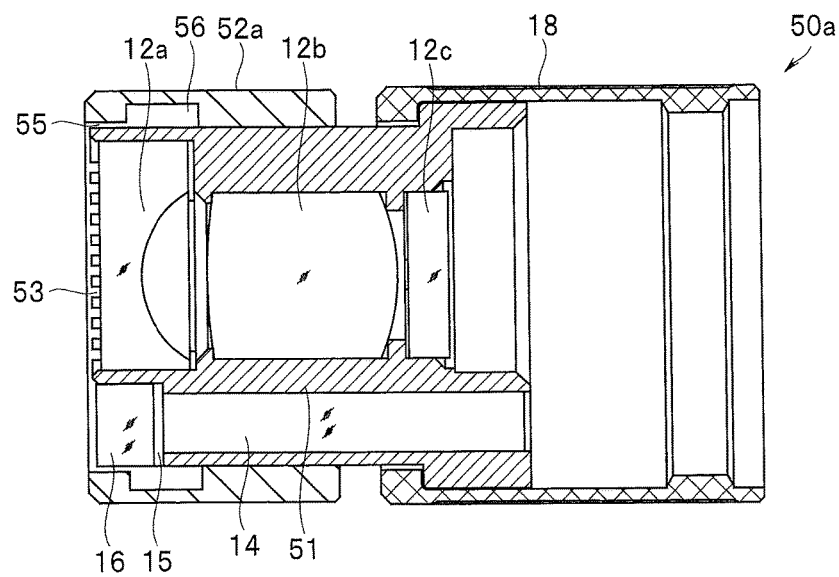
FIG. 17 is a sectional view showing a configuration of an optical adapter in a modification 1 of the second embodiment.

FIG. 17 is a sectional view showing a configuration of an optical adapter in the modification 1 of the second embodiment. Note that, in FIG. 17, components same as the components shown in FIG. 16 are denoted by the same reference numerals and signs and explanation of the components is omitted.

As shown in FIG. 17, an optical adapter 50a is configured using a cover member 52a instead of the cover member 52 shown in FIG. 16.

In the cover member 52a, a very small gap 55 is provided between the cover member 52a and the lens frame 51 and between the cover member 52a and the cover glass 16. A space 56, in which liquid such as oil can be accumulated, is provided on a proximal end side of the gap 55. Note that, in this modification, the space 56 is provided in the cover member 52a. However, the space 56 is not limited to this. A space for accumulating liquid such as oil may be provided in a predetermined position of the lens frame 51 formed on the proximal end side of the gap 55. The other components are the same as the components of the optical adapter 50 in the second embodiment.

A droplet adhering to the objective lens 12a is sucked up to the cover member 52a side by the capillary action due to the plurality of grooves 53 provided in the lens frame 51. Liquid sucked up in this way is sucked up by the capillary action due to the gap 55 provided between the cover member 52a and the lens frame 51. The liquid sucked up in this way can be accumulated in the wide space 56 inside the cover member 52a.

In this way, in the optical adapter 50a, the wide space 56 is provided on the inside of the cover member 52a. The liquid sucked up by the capillary action due to the plurality of grooves 53 and the gap 55 is accumulated in the wide space 56. The space 56 is provided on the inside of the cover member 52a and can be set wider than the space 54 shown in FIG. 16. Therefore, the optical adapter 50a can discharge a larger amount of the liquid than the optical adapter 50 shown in FIG. 16.

Therefore, with the optical adapter 50a in the modification 1, it is possible to remove a larger amount of the droplet than the optical adapter 50 in the second embodiment.
(Modification 2)

A modification 2 of the second embodiment is explained.

Figure 18:
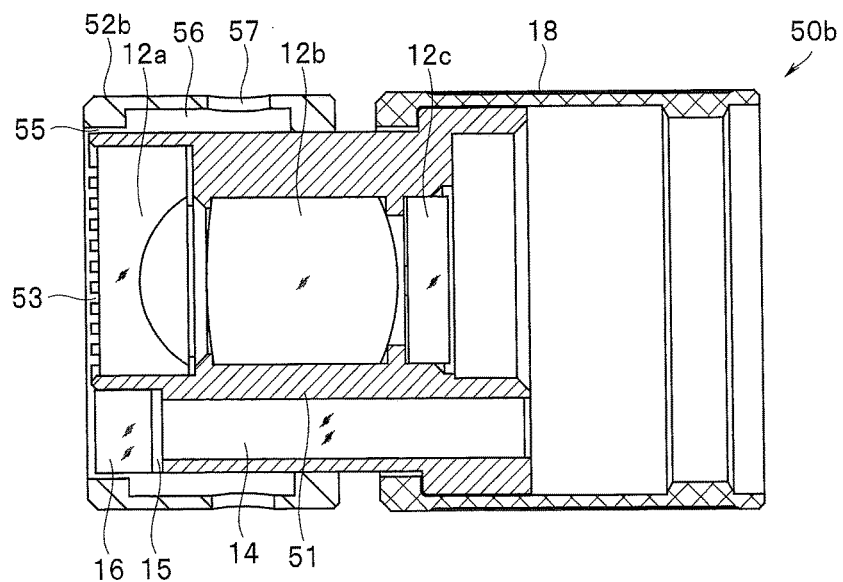
FIG. 18 is a sectional view showing a configuration of an optical adapter in a modification 2 of the second embodiment.

FIG. 18 is a sectional view showing a configuration of an optical adapter in the modification 2 of the second embodiment. Note that, in FIG. 18, components same as the components shown in FIG. 17 are denoted by the same reference numerals and signs and explanation of the components is omitted.

As shown in FIG. 18, an optical adapter 50b is configured using a cover member 52b instead of the cover member 52a shown in FIG. 17.

In the cover member 52b, a plurality of holes 57 communicating with the space 56 are provided on a side surface. Note that, in an example shown in FIG. 18, two holes 57 are provided on the side surface of the cover member 52b. However, at least one hole only has to be provided on the side surface of the cover member 52b. A size of the holes 57 is not particularly limited. The holes 57 only have to have a size suitable for collecting liquid such as oil accumulated in the space 56. The other components are the same as the components of the optical adapter 50a in the modification 1.

As in the modification 1, a droplet adhering to the objective lens 12a is sucked up by the capillary action due to the plurality of grooves 53 and the gap 55 and accumulates in the space 56. A user inserts an instrument such as a swab for collecting the accumulated liquid into the holes 57 provided on the side surface of the cover member 52b and collects the liquid accumulated in the space 56.

In this way, in the optical adapter 50b, the holes 57 communicating with the space 56 are provided on the side surface of the cover member 52b to enable collection of liquid accumulated in the space 56 and cleaning in the space 56. By adopting such a configuration, when a large amount of the droplet adheres to the objective lens 12a and the space 56 is filled with the liquid sucked up by the capillary action, the liquid in the space 56 can also be discharged to an outside of the cover member 52b from the holes 57.

Therefore, with the optical adapter 50b in the modification 2, it is possible to collect the liquid in the space 56 and clean the space 56. Further, it is possible to remove a larger amount of the droplet than the optical adapter 50 in the second embodiment.
(Modification 3)

A modification 3 of the second embodiment is explained.

Figure 19:
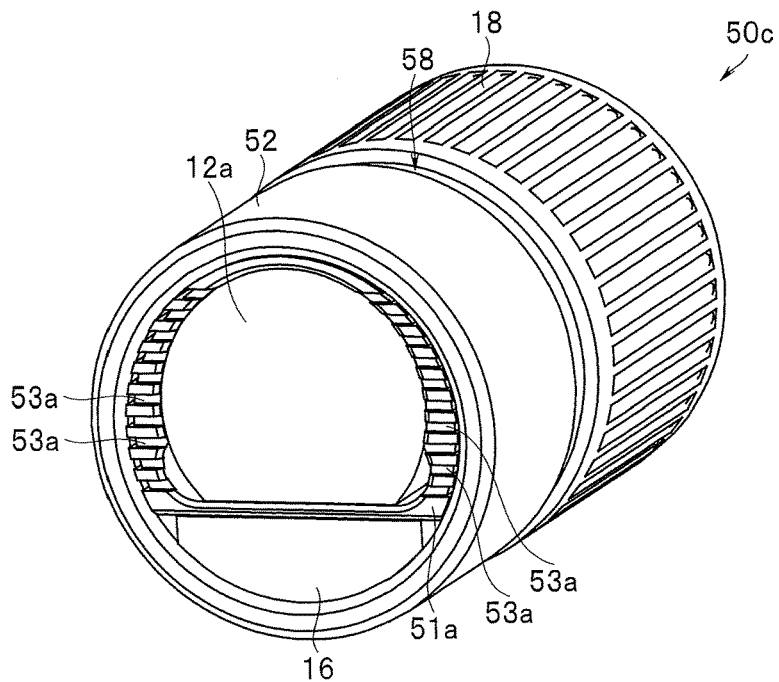
FIG. 19 is a perspective view showing a configuration of an optical adapter in a modification 3 of the second embodiment.
Figure 20:
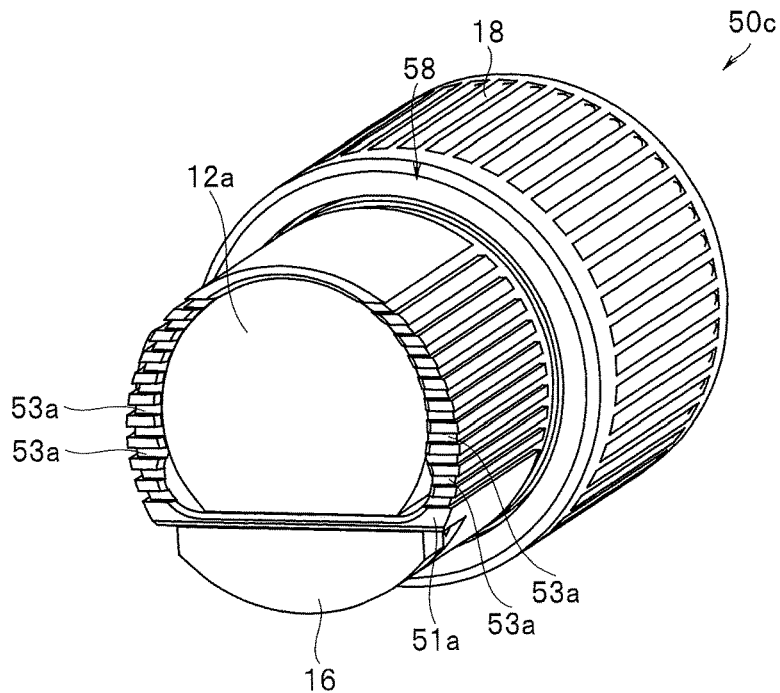
FIG. 20 is a perspective view showing a configuration at the time when a cover member of the optical adapter shown in FIG. 19 is detached.

FIG. 19 is a perspective view showing a configuration of an optical adapter in the modification 3 of the second embodiment. FIG. 20 is a perspective view showing a configuration at the time when a cover member of the optical adapter shown in FIG. 19 is detached. Note that, in FIGS. 19 and 20, components same as the components shown in FIG. 15 are denoted by the same reference numerals and signs and explanation of the components is omitted.

As shown in FIGS. 19 and 20, an optical adapter 50c is configured using a lens frame 51a instead of the lens frame 51 shown in FIG. 15.

A plurality of grooves 53a are provided on a distal end face of the lens frame 51a. The plurality of grooves 53a are extended to the proximal end side of the cover member 52 in an insertion axis direction of a side surface of the lens frame 51a. That is, the plurality of grooves 53a are extended to a gap 58 between the cover member 52 and the retaining ring 18. The other components are the same as the components of the optical adapter 50 in the second embodiment.

Note that a configuration of the lens frame 51a is not limited to the configuration shown in FIG. 20. For example, as in FIG. 8, the plurality of grooves 53a provided on the side surface of the lens frame 51a may be extended to a predetermined position of the lens frame 51a without being extended to the gap 58. As in FIG. 10, the lens frame 51a may include a plurality of grooves in a circumferential direction of the lens frame 51a in addition to the plurality of grooves 53a extended in the insertion axis direction.

A droplet adhering to the objective lens 12a is sucked up by the capillary action due to the plurality of grooves 53a. The plurality of grooves 53a are extended to the gap 58 on the side surface of the lens frame 51a. Therefore, when a constant amount or more of the droplet adheres to the objective lens 12a, liquid sucked up by the capillary action is discharged to the gap 58 between the cover member 52 and the retaining ring 18.

Therefore, with the optical adapter 50c in the modification 3, it is possible to remove a larger amount of the droplet than the optical adapter 50 in the second embodiment.
(Modification 4)

A modification 4 of the second embodiment is explained.

Figure 21:
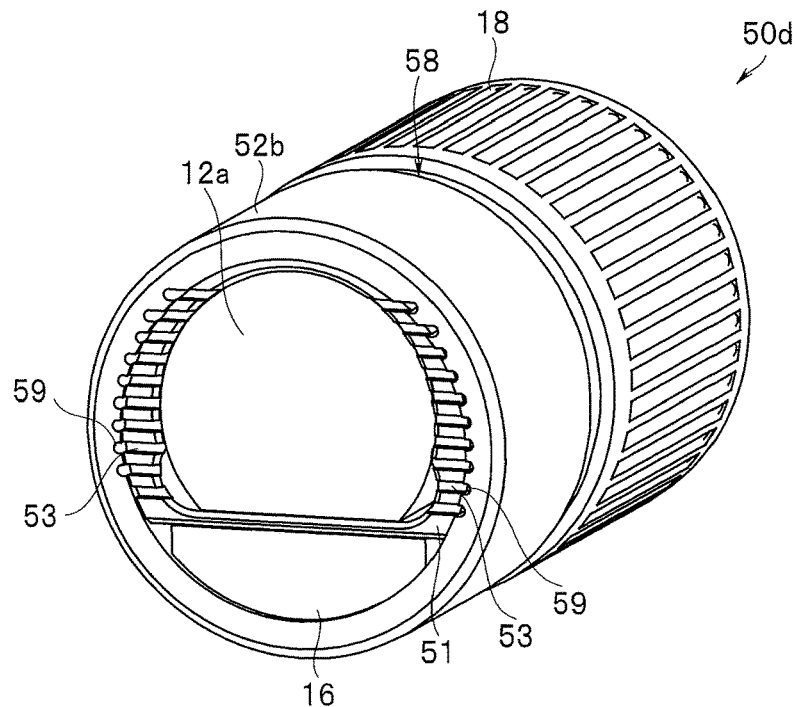
FIG. 21 is a perspective view showing a configuration of an optical adapter in a modification 4 of the second embodiment.
Figure 22:
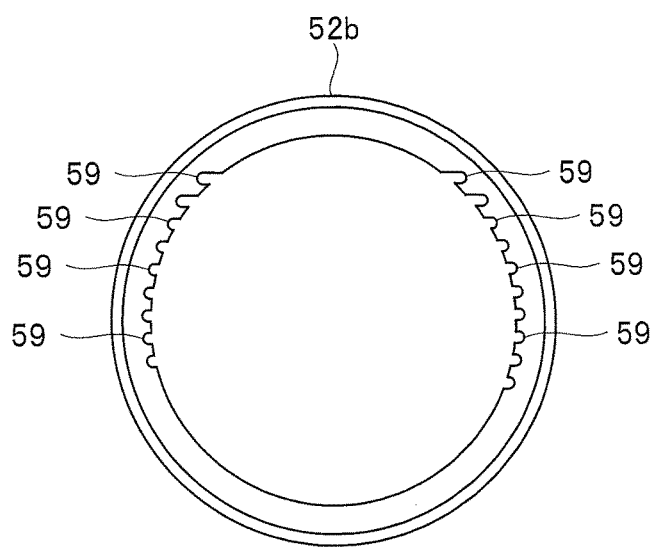
FIG. 22 is a front view showing a configuration of a cover member.

FIG. 21 is a perspective view showing a configuration of an optical adapter in the modification 4 of the second embodiment. FIG. 22 is a front view showing a configuration of a cover member. Note that, in FIG. 21, components same as the components shown in FIG. 15 are denoted by the same reference numerals and signs and explanation of the components is omitted.

As shown in FIG. 21, an optical adapter 50d is configured using a cover member 52b instead of the cover member 52 shown in FIG. 15.

On an inner circumferential surface of the cover member 52b, a plurality of grooves 59 are provided in positions opposed to the plurality of grooves 53 provided on the distal end face of the lens frame 51. The plurality of grooves 59 are extended to the proximal end side of the cover member 52b, that is, the gap 58 between the cover member 52b and the retaining ring 18. The other components are the same as the components of the optical adapter 50 in the second embodiment.

A droplet adhering to the objective lens 12a is sucked up to the cover member 52b side by the capillary action due to the plurality of grooves 53. Sucked-up liquid is sucked up by the capillary action due to the plurality of grooves 59 provided in the cover member 52b and accumulates in the plurality of grooves 59 (i.e., a gap between the lens frame 51 and the cover member 52b). Since the plurality of grooves 59 are extended to the gap 58 on the side surface of the lens frame 51a, when a constant amount or more of the droplet adheres to the objective lens 12a, the liquid sucked up by the capillary action is discharged to the gap 58 between the cover member 52 and the retaining ring 18.

Therefore, with the optical adapter 50d in the modification 4, it is possible to remove a larger amount of the droplet than the optical adapter 50 in the second embodiment.

(Modification 5)

A modification 5 of the second embodiment is explained below.

Figure 23:
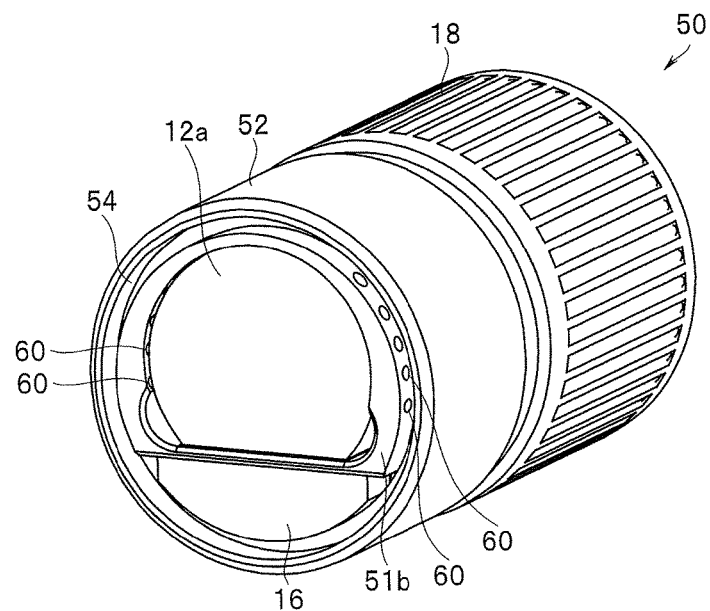
FIG. 23 is a perspective view showing a configuration of an optical adapter in a modification 5 of the second embodiment.
Figure 24:
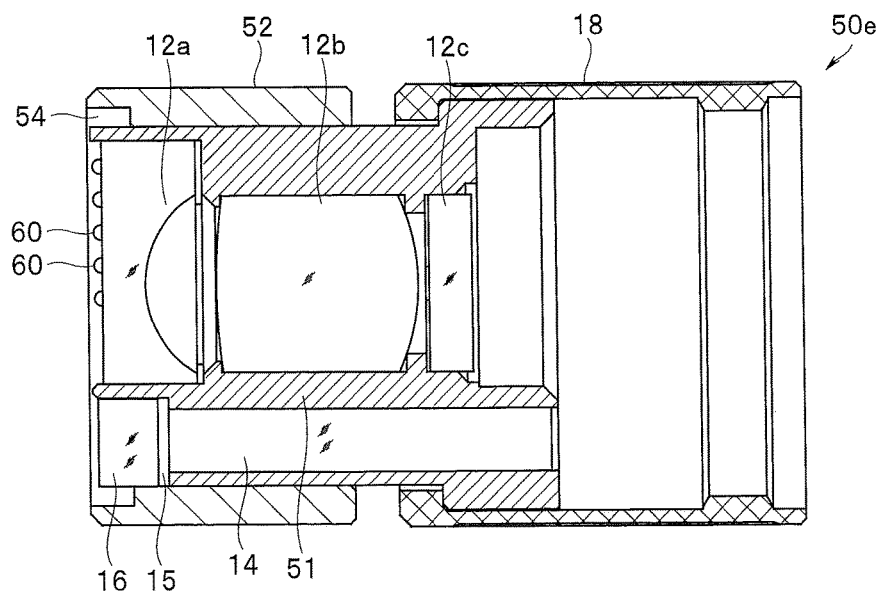
FIG. 24 is a sectional view showing the configuration of the optical adapter in the modification 5 of the second embodiment.

FIG. 23 is a perspective view showing a configuration of an optical adapter in the modification 5 of the second embodiment. FIG. 24 is a sectional view showing the configuration of the optical adapter in the modification 5 of the second embodiment. Note that in FIGS. 23 and 24, components respectively the same as the components shown in FIGS. 15 and 16 are denoted by the same reference numerals and signs and explanation of the components is omitted.

As shown in FIG. 23, an optical adapter 50e is configured using a lens frame 51b instead of the lens frame 51 shown in FIG. 15. In the lens frame 51b, a plurality of very small holes 60 piercing through the lens frame 51b from an inner circumferential surface to an outer circumferential surface on a distal end side on which the objective lens 12a is disposed are provided. As shown in FIG. 24, the plurality of holes 60 are respectively disposed in positions where parts of the holes 60 are exposed forward with respect to the side surface of the objective lens 12a on the inner circumferential surface side of the lens frame 51b. Note that the plurality of holes 60 are provided in a lateral direction in an example shown in FIG. 23. However, the plurality of holes 60 are not limited to this and may be provided in other directions. The other components are the same as the components of the optical adapter 50 in the second embodiment.

A droplet adhering to the objective lens 12a is sucked up from the inner circumferential surface to the outer circumferential surface of the lens frame 51b by the capillary action due to the plurality of holes 60 provided in the lens frame 51b. Liquid sucked up in this way can be accumulated in the space 54 between the cover member 52 and the lens frame 51b and between the cover member 52 and the cover glass 16.

Therefore, with the optical adapter 50e, as in the second embodiment, even when a large amount of the droplet such as oil adheres to the objective lens, it is possible to surely remove the droplet adhering to the objective lens.

(Modification 6)

A modification 6 of the second embodiment is explained.

Figure 25:
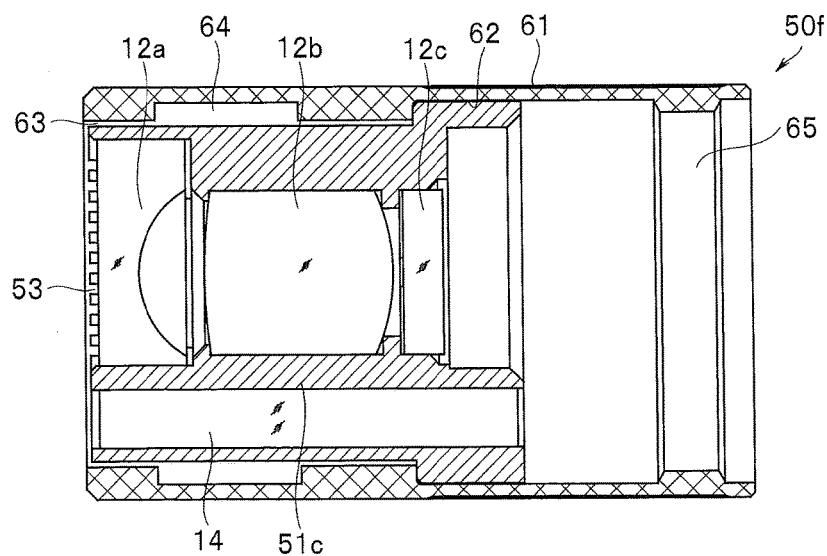
FIG. 25 is a sectional view showing a configuration of an optical adapter in a modification 6 of the second embodiment.
Figure 26:
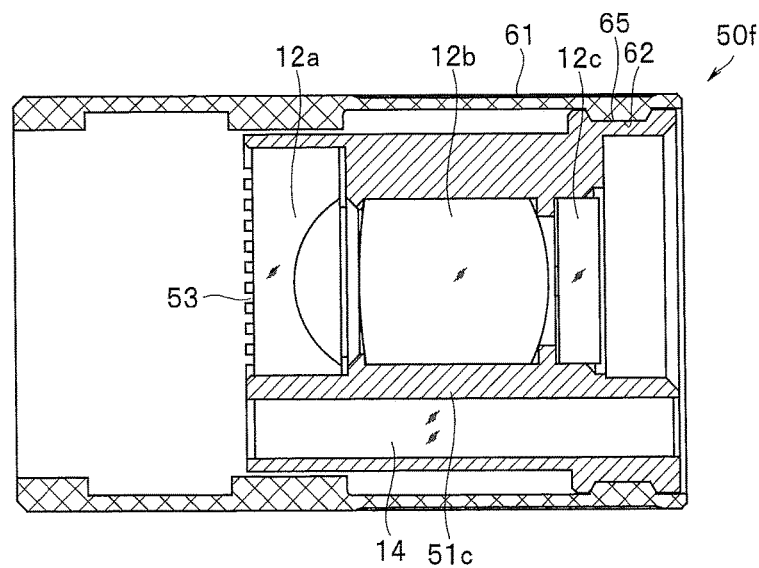
FIG. 26 is a sectional view showing a state in which a retaining ring is detached from a lens frame.
Figure 27:
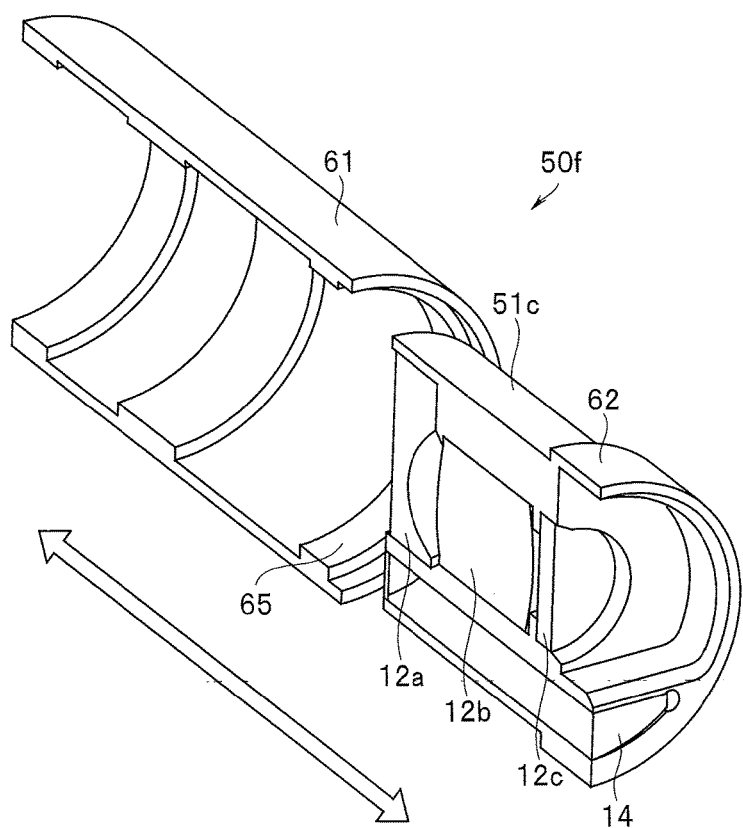
FIG. 27 is a sectional perspective view showing a configuration of an optical adapter in the modification 6 of the second embodiment.

FIG. 25 is a sectional view showing a configuration of an optical adapter in the modification 6 of the second embodiment. FIG. 26 is a sectional view showing a state in which a retaining ring is detached from a lens frame. FIG. 27 is a sectional perspective view showing the configuration of the optical adapter in the modification 6 of the second embodiment.

As shown in FIGS. 25 to 27, an optical adapter 50f is configured using a lens frame 51c instead of the lens frame 51 shown in FIG. 15. The optical adapter 50f includes a retaining ring 61 in which the cover member 52 and the retaining ring 18 shown in FIG. 15 are integrated.

In the lens frame 51c, the diffusing member 15 and the cover glass 16 are deleted from the lens frame 51 shown in FIG. 15. The lens frame 51c is fixed to a predetermined position of the retaining ring 61 by a screw mechanism 62 provided on the proximal end side.

On the distal end side of the retaining ring 61, a very small gap 63 is provided between the distal end side of the retaining ring 61 and the distal end side of the lens frame 51c. A wide space 64 is provided on the proximal end side of the gap 63. Note that the space 64 is provided in the retaining ring 61. However, the space 64 is not limited to this and may be provided on the lens frame 51c side.

With such a configuration, a droplet adhering to the objective lens 12a can be sucked up by the capillary action due to the plurality of grooves 53 and the gap 63 and accumulated in the space 64. A screw mechanism 65 is provided on the proximal end side of the retaining ring 61. The optical adapter 50f can be fixed to the distal end portion 8 of the scope unit 3 via the screw mechanism 65.

In this modification, the screw mechanism 62 of the lens frame 51c and the screw mechanism 65 of the retaining ring 61 are formed as the same screw mechanism such that the lens frame 51c and the retaining ring 61 can be attached and detached. For example, the screw mechanism 62 of the lens frame 51c forms a male screw and the screw mechanism 65 of the retaining ring 61 forms a female screw detachably attachable to the male screw.

A droplet adhering to the objective lens 12a is sucked up to the retaining ring 61 side by the capillary action due to the plurality of grooves 53 provided in the lens frame 51c. Liquid sucked up in this way is sucked up by the capillary action due to the gap 63 provided between the retaining ring 61 and the lens frame 51c. The liquid sucked up in this way can be accumulated in the wide space 64 inside the retaining ring 61.

The retaining ring 61 is detachably attachable to the lens frame 51c. Therefore, during an endoscopic inspection or after an end of the endoscopic inspection, the user can detach the retaining ring 61 from the lens frame 51c and collect the liquid such as oil sucked up by the capillary action and accumulated in the space 64 of the retaining ring 61 and clean the space 64 of the retaining ring 61 by, for example, wiping the liquid.

Therefore, with the optical adapter 50f in the modification 6, it is possible to collect the liquid in the retaining ring 61 and clean the retaining ring 61. Further, it is possible to remove a larger amount of the droplet than the optical adapter 50 in the second embodiment.

The present invention is not limited to the embodiments and the modifications explained above. Various changes, alterations, and the like are possible in a range in which the gist of the present invention is not changed.

What is claimed is:

1. An endoscope optical adapter comprising:
   an objective lens for observation;
   a lens frame configured to hold the objective lens;
   a cover member fixed to an outer circumference of the lens frame and extended to an inner side to surround the objective lens;
   an attaching and detaching member provided with a screw mechanism, the attaching and detaching member being coupled to a proximal end side of the lens frame and detachably attachable to a distal end portion of an endoscope; and a path for discharging a droplet adhering to a distal surface of the objective lens, wherein the path includes a first groove, the first groove being configured to allow the droplet adhered to the distal surface of the objective lens to move from a center of the objective lens toward an outer circumference of the objective lens, an opening of the first groove, in a front view of the distal surface of the objective lens, being formed in an arc shape at least partially along a shape of the outer circumference of the objective lens in a length direction of the first groove, a bottom of the first groove being formed at a position which is recessed with respect to a distal end face of the cover member and which is recessed with respect to the distal surface of the objective lens, and the arc-shaped first grove comprises:

an inner surface configured by an outer circumferential surface of the objective lens;

an outer side surface configured by the cover member; and the bottom configured by the lens frame.

2. The endoscope optical adapter according to claim 1, wherein the opening of the first groove, in the front view of the distal surface of the objective lens, is provided in a half circumference or more of a peripheral section of the objective lens.

3. The endoscope optical adapter according to claim 1, further comprising a plurality of second grooves different from the first groove, wherein the plurality of second grooves are formed on one of a distal end face of the lens frame and the cover member, wherein the plurality of second grooves are configured to allow the droplet temporally accumulated in the first groove to be drawn into the plurality of second grooves.

4. The endoscope optical adapter according to claim 3, wherein a shape of a cross section of each of the plurality of second grooves is one of a V shape, a rectangular shape, and a semicircular shape, the cross section being orthogonal to an extending direction of each of the plurality of second grooves.

5. The endoscope optical adapter according to claim 3, wherein the plurality of second grooves have a tapered shape in which a width of each of the plurality of second grooves increases from an inner circumference to an outer circumference of the distal end face of the lens frame or the cover member.

6. The endoscope optical adapter according to claim 3, wherein the plurality of second grooves are extended in an insertion axis direction to one of a predetermined position of a side surface of the lens frame and a predetermined position of a side surface of the cover member.

7. The endoscope optical adapter according to claim 3, wherein the plurality of second grooves are extended in an insertion axis direction to one of the proximal end side of the lens frame and a proximal end side of the cover member.

8. The endoscope optical adapter according to claim 3, wherein the plurality of second grooves are extended in parallel with each other in the front view of the front surface of the objective lens.

9. The endoscope optical adapter according to claim 3, wherein a depth position of each of the plurality of second grooves is located so as to be recessed with respect to the distal surface of the objective lens.

10. The endoscope optical adapter according to claim 1, wherein the objective lens includes a plurality of lenses and the lens frame holds the plurality of lenses.

11. The endoscope optical adapter according to claim 10, wherein the inner side surface of the arc-shaped first groove is configured by an outer circumferential surface of a distal-most lens of the plurality of lenses.

* * * * *